United States Patent [19]

Barnett et al.

[11] Patent Number: 5,302,722
[45] Date of Patent: Apr. 12, 1994

[54] 3-CARBOXY-PYRROLE DERIVATIVES

[75] Inventors: Charles J. Barnett, Indianapolis; Thomas M. Wilson, Speedway, both of Ind.

[73] Assignee: Eli Lilly and Company, Indianapolis, Ind.

[21] Appl. No.: 67,204

[22] Filed: May 25, 1993

Related U.S. Application Data

[62] Division of Ser. No. 961,595, Oct. 15, 1992, Pat. No. 5,254,716.

[51] Int. Cl.⁵ .................................. C07D 207/12
[52] U.S. Cl. .................................. 548/531; 548/543
[58] Field of Search .......................... 548/531, 543

[56] References Cited

U.S. PATENT DOCUMENTS 5,008,391  4/1991  Barnett et al. .................. 546/243

OTHER PUBLICATIONS

Zelle, R. E., *Synthesis*, 1991, No. 11: 1023–1026.
Barnett, et al., *Tetrahedron Letters*, 30:6291–6294 (1989).
Miwa, et al., *J. Med. Chem.*, 34:555–560 (1991).
Larsen, C., et al., *Liebigs Ann. Chem.*, 1989:819–823.
*The Chemistry of Functional Groups*, 2, part 2:1295–1296 (Patai, S., Ed., 1989).

*Primary Examiner*—Mukund J. Shah
*Assistant Examiner*—Y. N. Gupta
*Attorney, Agent, or Firm*—Steven A. Fontana; Leory Whitaker

[57] ABSTRACT

This invention relates to intermediates and processes thereto, for the preparation of 5,6-dihydropyrro[2,3-d] pyrimidines which are useful for the treatment of susceptible neoplasms.

14 Claims, No Drawings

3-CARBOXY-PYRROLE DERIVATIVES

This application is a division of application Ser. No. 07/961,595, filed Oct. 15, 1992 now U.S. Pat. No. 5,254,716.

BACKGROUND OF THE INVENTION

This invention relates to the fields of pharmaceutical and organic chemistry, and provides novel intermediates which are useful in the synthesis of 5,6-dihydropyrrolo[2,3-d]pyrimidine antimetabolites of the antifolate type. This invention also relates to processes for the preparation of such intermediates.

Substituted pyrrolo[2,3-d]pyrimidine-based antifolates have been used for a number of years as chemotherapeutic agents in the treatment of cancer. One such drug, methotrexate, is now one of the most widely used anticancer drugs; and many other compounds in the folic acid family have been synthesized, tested and discussed in the chemical and medical literature. The compounds have various activities at the enzymatic level; they inhibit such enzymes as dihydrofolate reductase, folate polyglutamate synthetase, glycinamide ribonucleotide formyltransferase and thymidylate synthase.

A problem inherent to pyrrolo[2,3-d]pyrimidine synthesis is preparing the reduced form; the 5,6-dihydro analogue. Using standard reduction methods, this reaction usually proceeds, if at all, with great difficulty. The pyrrolo[2,3-d]pyrimidine chromophore is found to be resistant to catalytic hydrogenation over palladium and platinum oxide catalysts. In addition, it is resistant to reduction by triethylsilane in trifloroacetic acid as well as reduction under conditions such as contact with hydrogen gas at 1250 psi in the presence of a 10% palladium-on-carbon catalyst.

Recently, a series of pyrrolopyrimidine derivatives has been disclosed as antifolate compounds having antineoplastic activity. See e.g., European Patent Publication 334 636, (Akimoto, et al.,) and U.S. Pat. No. 4,997,838 (also, Akimoto et al.). Akimoto has shown a possible solution to this reduction problem by utilizing an isopropyloxymethyl protecting group at the 3-position and a benzyl group at the 7-position of the pyrrolopyrimidine. Although the presence of the protecting groups permits the preparation of 5,6-dihydropyrrolopyrimidines via catalytic hydrogenation, this synthesis is quite expansive, as the requisite protected substrate requires many steps to produce from commercially available materials.

The present invention provides novel intermediates for the preparation of 5,6-dihydropyrrolo[2,3-d]pyrimidine antifolate-type antimetabolites, and novel processes for the preparation of those intermediates. The processes are less laborious and thus provide an inexpensive means to prepare 5,6-dihydropyrrolo[2,3-d]pyrimidines.

SUMMARY OF THE INVENTION

The present invention relates to compounds of the following formulas:

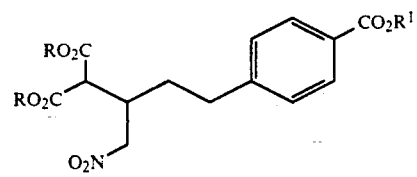

wherein

R is the same $C_1-C_4$ alkyl or phenyl which may be substituted; and $R^1$ is H, $C_1-C_4$ alkyl, phenyl which may be substituted or benzyl; and

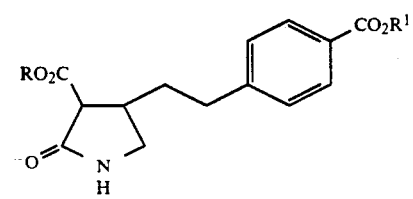

wherein

R is $C_1-C_4$ al or phenyl which may be substituted; and $R^1$ is H, $C_1-C_4$ alkyl, phenyl which may be substituted or benzyl; or a salt thereof; and

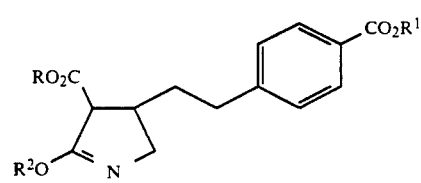

wherein

R is $C_1-C_4$ alkyl or phenyl which may be substituted; and $R^1$ is H, $C_1-C_4$ alkyl, phenyl which may be substituted or benzyl; and $R^2$ is $C_1-C_4$ alkyl; or a salt thereof; and

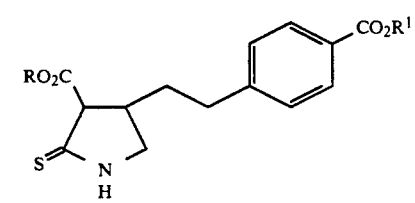

wherein

R is $C_1-C_4$ alkyl or phenyl which may be substituted; and $R^1$ is H, $C_1-C_4$ alkyl, phenyl which may be substituted or benzyl; or a salt thereof This invention also relates to a process for preparing a 5,6-dihydropyrrolo-[2,3-d]pyrimidine of the formula

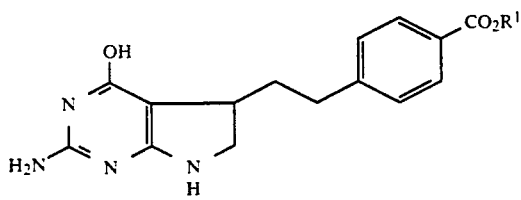

wherein
R¹ is H, C₁-C₄ alkyl, phenyl which may be substituted or benzyl; or a salt thereof, which comprises
(a) reacting a compound of formula II

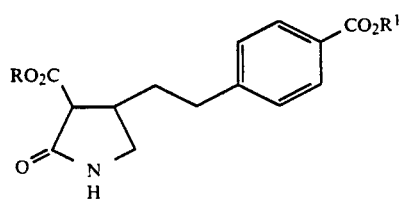

wherein
R is C₁-C₄ alkyl or phenyl which may be substituted; and
R¹ is H, C₁-C₄ alkyl, phenyl which may be substituted or benzyl; or a salt thereof, with a sulfurization agent; and
(b) cyclizing the reaction product from step (a) with guanidine.

Furthermore, the invention relates to the process described above which, when R¹ is t-butyl, includes the additional step of treating the reaction product from step (a) with a strong acid prior to the cyclization step.

DETAILED DESCRIPTION OF THE INVENTION

The present invention pertains to novel intermediate compounds which are valuable for the preparation of 5,6-dihydropyrrolo[2,3-d]pyrimidine derivatives, and processes thereto.

The 5,6-dihydropyrrolo[2,3-d]pyrimidines prepared via the intermediates of this invention, particularly a compound of formula VI

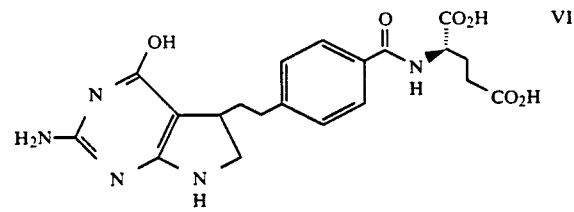

have an inhibitory effect on one or more enzymes which utilize folic acid and, in particular, metabolic derivatives of folic acid, as cofactors. Neoplasms in animals which depend upon such enzymes for growth are susceptible to treatment when an effective amount of this type of compound is administered to such an animal. Thus, the intermediates of this invention, and processes thereto, are useful for the preparation of 5,6-dihydropyrrolo[2,3-d] pyrimidines which may be utilized for the treatment of susceptible neoplasms in animals, particularly humans In formula VI, the configuration of the L-glutamic acid residue is shown unambigously. The glutamic acid residue for all compounds disclosed herein is in the L-configuration. In addition, an asymmetric center is located at the 5-position of the 5,6-dihydropyrrolo[2,3-d]pyrimidine ring system in formulas V and VI, and at the 4-position of formulas II-IV. If desired, the individual enantiomers (formula II-V compounds) or diastereomers (formula VI compounds) may be separated by standard methods for resolution. Each of the enantiomers/diastereomers which can be separated by such a method is included in this invention.

Furthermore, an asymmetric center is located at the 3-position of formulas II-IV. However, this center is eliminated upon cyclization with guanidine and the configuration does not influence the direction or efficiency of the process.

Compounds of formulas V and VI exist in tautomeric equilibrium with the corresponding 4(3H)-oxo compounds. For illustrative purposes, the equilibrium for the pyrrolopyrimidine system are shown below:

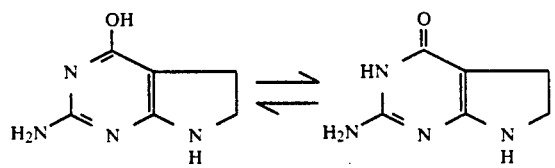

For convenience, the 4-hydroxy form is depicted for formulas V and VI, and the corresponding nomenclature is used throughout this specification. However, it is understood that such depictions include the corresponding tautomeric 4(3H)-oxo forms.

Furthermore, compounds of formula IV exist in tautomeric equilibrium with the corresponding 2-mercapto compounds. For convenience, the 2-thiocarbonyl form is depicted for formula IV, and the corresponding nomenclature is used throughout this specification. However, it is understood that such depictions include the corresponding tautomeric 2-mercapto forms.

The term "C₁-C₄ alkyl" refers to the straight or branched aliphatic chains of 1-4 carbon atoms, including methyl, ethyl, propyl, isopropyl, n-butyl, isobutyl, secbutyl and tert-butyl (t-butyl).

The term "phenyl which may be substituted" denotes an unsubstituted or substituted phenyl residue, optionally having one or two substituents selected from halo, nitro, C₁-C₄ alkyl and C₁-C₄ alkoxy.

The term "halo" refers to bromo, chloro, fluoro and iodo.

The term "C₁-C₄ alkoxy" represents a C₁-C₄ alkyl group attached through an oxygen bridge, such as, for example, methoxy, ethoxy, n-propoxy, isopropoxy and the like.

The carboxyl protecting groups of R and R¹, when R¹ is not H, denote groups which generally are not found in final therapeutic compounds, but which are intentionally introduced during a portion of the synthetic process to protect a group which otherwise might react in the course of chemical manipulations, and is then removed at a later stage of the synthesis. Since compounds bearing such protecting groups are of importance primarily as chemical intermediates (although some derivatives also exhibit biological activity), their precise structure is not critical. Numerous reactions for the formation and removal of such protecting groups are described in a number of standard works including, for example, "Protective Groups in Organic Chemistry", Plenum Press, (London and New York, 1973); Greene, Th. W., "Protective Groups in Organic Synthesis", Wiley, (New York, 1981); and "The Peptides", Vol. 1, Schroöder and Lubke, Academic Press, (London and New York, 1965).

Representative R carboxyl protecting groups include $C_1$–$C_4$ alkyl or phenyl which may be substituted. Representative $R^1$ groups, when $R^1$ is not H, include $C_1$–$C_4$ alkyl, phenyl which may be substituted or benzyl. These groups are selectively removable under sufficiently mild conditions so as to not disrupt the desired structure of the molecule.

When two R groups are present, as with the compounds of formula I, it is preferred that both R groups are the same carboxyl protecting group. However, when carboxyl protecting groups R and $R^1$ are simultaneously present, it is preferred that they are not the same group. Preferred R groups are $C_1$–$C_4$ alkyl, especially ethyl; when R is ethyl, the preferred $R^1$ group is t-butyl.

The invention includes salts of the compounds defined by the above formulas, especially when $R^1$ is H. A particular compound of this invention can possess a sufficiently acidic, a sufficiently basic, or both functional groups, and accordingly react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromo-phenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4- dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate. The potassium and sodium salt forms are particularly preferred.

Of course, when the intermediates of this invention are converted to final, pharmaceutically active compounds, those compounds may also be in the form of a salt, but that salt must be pharmaceutically acceptable.

The preferred starting materials for preparing compounds of the present invention are t-butyl-4-iodobenzoate (formula VII below wherein $R^1$ is t-butyl) and allyl alcohol (2-propen-1-ol; formula VIII). Some of the starting materials, such as allyl alcohol, are commercially available (e.g. Aldrich Chemical Company) Those which are not commercially available can be prepared by conventional organic chemistry methods using commerically available reagents.

One will note that the desired $R^1$ carboxyl protecting group, particularly $C_1$–$C_4$ alkyl, phenyl which may be substituted or benzyl, is present on the 4iodobenzoate starting material prior to the first step of the process for preparing compounds of formulas I–IV. Use of a preferred $R^1$ group, $C_1$–$C_4$ alkyl, especially t-butyl, permits survival of this protecting group during the relatively harsh reduction of the nitro group on formula 1 compounds (Equation 2).

When selecting starting materials, $R^1$ may also be hydrogen or $R^1$ may be converted to hydrogen prior to the sulfurization step shown in Equation 3. It is best, however, to protect this carboxyl group with a preferred $R^1$ protecting group.

The first step to synthesize the compounds of the present invention requires reacting a compound of formula VII with a formula VIII compound in an inert or substantially inert polar solvent or mixture of solvents in the presence of a palladium catalyst, a phase transfer agent, and a base such as sodium bicarbonate and the like. This Heck-type reaction, which produces compounds of formula IX, is known in the art (see, e.g. Heck, Org. React., 27: 345 (1982); Taylor, et al., J. Org. Chem . 57: 3298-3225 (1992); Akimoto, et al., EP 402 903 (1990); and Varma, et al., U.S. Pat. No. 4,711,900), and is depicted below in Equation 1.

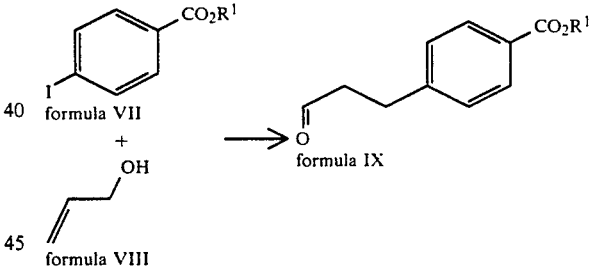

Suitable solvents are any polar solvent, or mixture of solvents, which will remain inert or substantially inert under reaction conditions. Preferred solvents include acetonitrile, N,N-dimethylformamide, toluene and N-methylpyrrolidone. Of these, N,N-dimethylformamide is especially preferred.

The palladium catalysts employed are those known in the art for the reaction of aryl halides and allylic alcohols. See, e.g.: Metpoler, et al., J. Org. Chem., 41: 265 (1976); Chalk, et al., J. Org. Chem., 41: 1206 (1976); and Arai, et al., J. Heterocyclic Chem., 15: 351 (1978). A preferred catalyst is palladium acetate.

A phase transfer agent, combined with a base such as sodium bicarbonate and the like, allows the reaction to proceed at ambient temperatures as disclosed by Jeffery, J., Chem. Soc. Chem. Commun., 1287-1289 (1984). Suitable phase transfer agents include quarternary ammonium salts such as tetrabutylammonium hydrogen sulfate, trioctylmethylammonium chloride, tetrabutylammonium chloride and tetrabutylammonium bromide. Tetrabutylammonium bromide is preferred.

The amount of reactants and reagents, the temperature employed and the length of time that is required to effect coupling is known in the art and is apparent to a skilled organic chemist (see, e.g., Example 1).

The second, third and fourth steps, respectively, in synthesizing the compounds of the present invention, require condensation of a compound of formula IX with a diethyl malonate (forming a formula X compound), converting the resulting malonate to a nitrodiester (a formula I compound) and then forming a formula II compound by hydrogenating the nitrodiester compound. The reaction sequence is depicted in Equation 2.

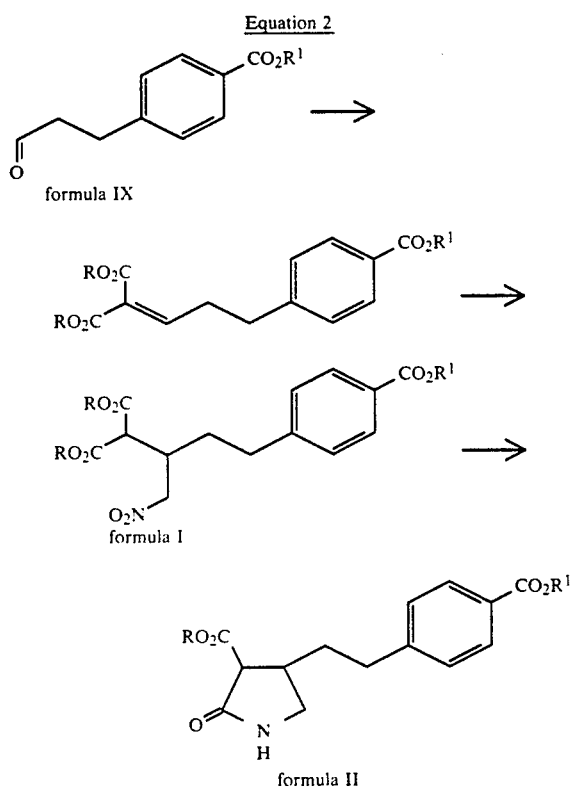

wherein R and $R^1$ are as defined supra.

The first step of Equation 2 involves reacting a formula IX compound with a di($C_1$-$C_4$) alkyl or optionally substituted diphenyl malonate, in the presence of a titanium IV catalyst and py ridine, in an appropriate solvent.

It is during this step that the carboxyl protecting group designated R is established. Preferably, R is $C_1$-$C_4$ alkyl, but not t-butyl when $R^1$ t-butyl. It is further preferred that, in formula X and formula I compounds, both R groups are the same carboxyl protecting group. This step, known in the art as a Knoevenagel condensation, is driven by a catalyst such as titanium IV halides, particularly titanium IV chloride. See, e.g., Lehnert, W., *Tetrahedron Letters*, 54: 4723-4 (1970).

Typically, the solvent employed in the first step of Equation 2 should be an ether which will remain inert under conditions necessary for accomplishing condensation. Suitable solvents include dioxane and tetrahydrofuran, with the latter being preferred.

Other parameters necessary for the completion of this step are described in the art. (See, e.g., Lehnert, supra).

The second step in Equation 2, i.e., reacting a compound of formula X with nitromethane in the presence of a catalyst such as 1,8-diazabiclyclo[5.4.0]undec-7-ene (DBU), and the like, in a suitable solvent, provides compounds of formula I. This reaction also is known in the art and is described in Ono, et al., *Synthesis*, 226-7, (March, 1984).

Suitable solvents for this step are any polar solvent, or mixture of solvents, which will remain inert or substantially inert under reaction conditions Preferred solvents are dipolar, aprotic solvents, especially acetonitrile and N,N-dimethylformamide.

In the third step of Equation 2, formula I compounds are catalytically hydrogenated, in the presence of suitable solvent, to form compounds of formula II. In this reaction, which is generally known in the art, hydrogen gas is the preferred reducing agent.

Suitable hydrogenation catalysts include noble metals and oxides such as palladium, platinum and rhodium oxide on a support such as carbon or calcium oxide. However, palladium-on-carbon and platinum-on-carbon are preferred, and platinum oxide is especially preferred.

Solvents for this reaction are those solvents or mixture of solvents which remain inert or substantially inert throughout the reaction Typically, alcohols such as methanol, 1-propanol, 2-propanol, and especially, ethanol, are suitable solvents.

The compounds of formulas I and II are novel and valuable as intermediates which can be used in the preparation of 5,6-dihydropyrrolo[2,3-d]pyrimidine derivatives which are useful antineoplastic agents.

Next, formula II compounds are sulfurized to form a thiolactam (formula IV), and cyclized to form compounds of formula V. This aspect of the process is novel and is depicted in Equation 3.

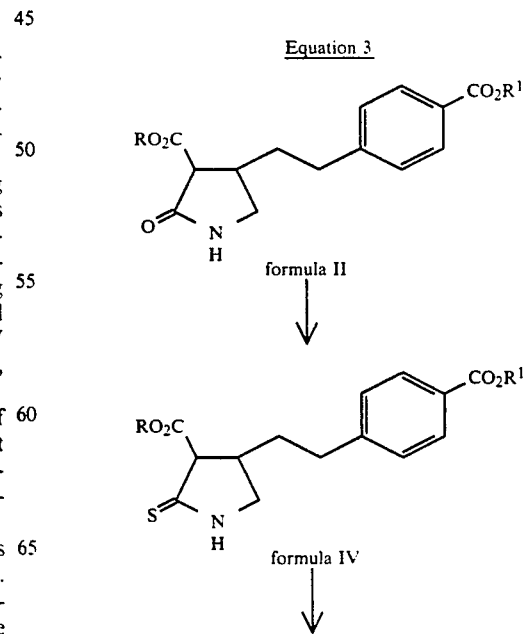

-continued
Equation 3

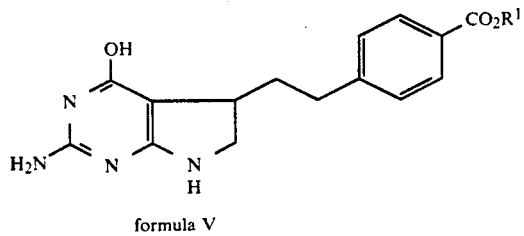

formula V wherein R and R[1] are as defined above.

The first step of Equation 3 involves the sulfurization of a compound of formula II, which forms compounds of formula IV. Although a number of sulfurization agents, such as Lawesson s reagent (see, e.g., *Organic Synthesis Highlights*, Mulzer, et al., (Weinhein and New York, 1991), may be used in this step, sulfurization is preferably accomplished using phosphorous pentasulfide.

The amount of sulfurization agent employed is suitably an amount sufficient to replace the 2-carbonyl moiety on the pyrrolidine ring by thiocarbonyl. Generally, from about one equivalent of sulfurization agent per equivalent of pyrrolidine is employed Preferably, an excess of sulfurization agent is used.

The first step shown in Equation 3 is accomplished in the presence of a suitable inert, or substantially inert, solvent, or mixture of solvents. A single, inert solvent such as tetrahydrofuran is preferred.

The temperature employed in this step is sufficiently elevated to effect completion of the sulfurization reaction. Typically, a temperature in the range from about 50° to about 70° C. is sufficient, and a temperature of about 60° C. is preferred.

The length of time for this sulfurization step to occur can vary. The reaction generally requires from about a few minutes to about a few hours. The optimal reaction time can be determined by monitoring the progress of the reaction by conventional chromatographic techniques such as thin layer chromotography, high performance liquid chromatography or column chromatography.

In the second step of this novel process (Equation 3), the reaction product from the step (a) (a formula IV compound) is reacted with guanidine, in an appropriate solvent, and forms a compound of formula V. For this cyclization step to occur, guanidine may be supplied as a salt, but it must first be converted to the free base via neutralization with a base. Thus, it is preferred to employ guanidine free base in this step of the reaction.

Appropriate solvents for the second step reaction include any solvent, or mixture of solvents, which will remain inert, or substantially inert, under reaction conditions. Especially, appropriate solvents include $C_1$–$C_4$ aliphatic alcohols such as methanol, ethanol, 1-propanol, 2-propanol, 1-butanol, 2-butanol and 2 methyl-2-propanol. Of these, ethanol is preferred.

Cyclization can occur over a broad range of substrate (a formula IV compound) concentrations. Typically, a concentration in the range from about 0.002 to about 10 molar is adequate, while a concentration of about 0.1 molar is more appropriate Suitable amounts of guanidine are those which are sufficient to react with all of a formula IV compound from step one of the reaction shown in Equation 3. Generally, from about one equivalent to an excess of guanidine per equivalent of a formula IV compound is employed. Preferably, an excess of guanidine is used.

Typically, this step proceeds in short periods of time at elevated temperatures, but the length of time will vary with the reaction conditions employed This cyclization reaction requires about 10 to about 30 minutes to proceed when run at the preferred temperature of about 50° C. However, this reaction may be run in a temperature range from about 30° C. to about 70° C.

Each step of the novel process depicted in Equation 3 may be individually run wherein each reaction product is isolated and purified. The products of this process, compounds of formula IV also are novel and are useful as intermediates for the preparation of 5,6-dihydropyrrolo[2,3-d]pyrimidines. Alternatively, it is preferred that the steps shown in Equation 3 are combined into a one-pot process comprising reacting a compound of formula II with a sulfurization agent and cyclizing the reaction product from the immediately preceding step by reacting that reaction product with guanidine.

When R[1] is t-butyl, an additional step is included in the process. This preferred process is depicted in Equation 4.

Equation 4

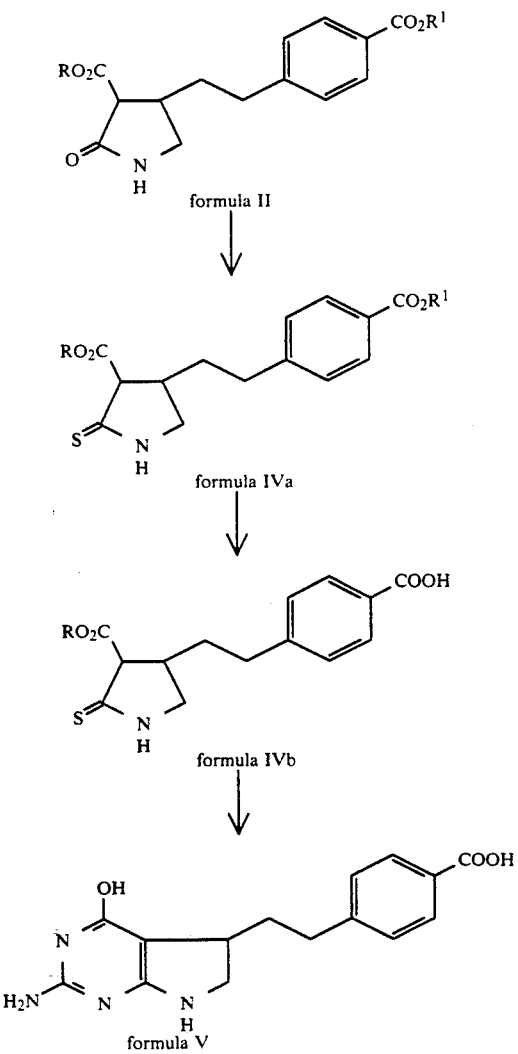

wherein R is as defined above and R[1] is t-butyl.

In Equation 4, the selection of t-butyl as the $R^1$ substituent allows for the conversion of this protecting group to the acid via an acid catalyst (step 1). Suitable acid catalysts can be any strong organic or inorganic acid which will facilitate the removal of the t-butyl protecting group from the benzoic acid moiety of a formula IVa compound. Such acid catalysts are well known in the art. See e.g., *Protective Groups in Organic Chemistry*, J. G. W. McOmie, Ed., Plenum Press (New York 1973); and T. W. Green, *Protective Groups in Organic Synthesis*, John Wiley and Sons (New York 1981). However, the preferred acid catalyst is triflouroacetic acid, especially when used in substantial excess per equivalent of substrate present.

Generally, this step of the reaction takes place nearly instantaneously, but the length of time required depends upon the choice of acid catalyst and its effectiveness in the process.

Although other $C_1-C_4$ alkyl substituents could be removed to form the acid, the presence of t-butyl as the $R^1$ substituent permits this removal without hydrolysis or displacement, leaving the R substituent undisturbed. By converting the $R^1$ substituent while leaving the R substituent as originally selected, cyclization at the desired location is favored and the potential for guanidine to react with the $R^1$ protected carboxyl group is eliminated.

Other than the reduction step described above, the other steps of Equation 4, including sulfurization of a formula II compound to form a formula IVa compound and the cyclization with guanidine, are carried out using the same methods, including the preferred methods, as described for these steps following Equation 3.

Each step of the novel process depicted in Equation 4 may be individually run wherein each reaction product is isolated and purified Alternatively, it is preferred that the steps shown in Equation 4 are carried out in the same vessel.

Alternative to the processes described in Equations 3 and 4, a formula V compound is prepared by converting the 2-carbonyl group of a formula II compound to an iminoalkoxy (formula III) and cyclizing the formula III compound. This aspect of the process is depicted in Equation 5.

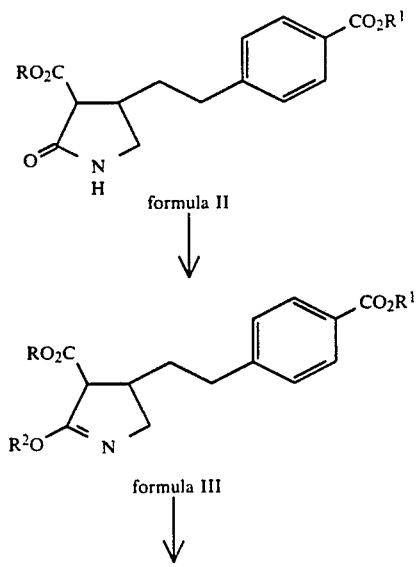

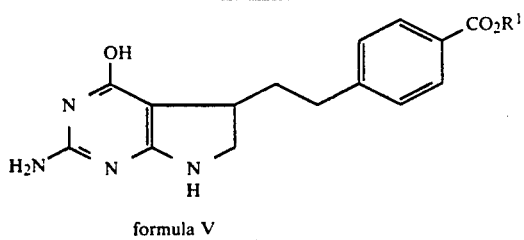

wherein R and $R^2$ are as defined above; and $R^1$ is H, $C_1-C_4$ alkyl, phenyl which may be substituted or benzyl.

In the first step of Equation 5, a compound of formula II is reacted with a trialkyloxonium tetrafluoroborate, in the presence of sodium bicarbonate, in a suitable solvent. This reaction is generally known in the organic chemical art (see, e.g., Barnett, et al., U.S. Pat. No. 5,008,391).

A suitable trialkyloxonium tetrafluoroborate is any which will convert the 2-carbonyl group of a formula II compound to the desired imminoester. Typical examples are trimethyloxonium tetraflouroborate, triethyloxonium tetrafluoroborate and the like.

The solvent employed in this step can be any solvent, or mixture thereof, which will remain inert or substantially inert under reaction conditions. Preferred solvents include halogenated hydrocarbons such as methylene chloride, chloroform, 1,2-dichloroethane and the like. Of these, chloroform is especially preferred.

The cyclization step of Equation 5 is carried out via the same method, including the preferred method, disclosed above for the cyclization step of Equation 3. Likewise, compounds of formula III are also novel and are useful as intermediates for the preparation of 5,6-dihydropyrrolo[2,3-d]pyrimidines.

Similar to the process described above in Equation 4, t-butyl may also be utilized as the preferred $R^1$ group of a formula III compound in Equation 5. Rather than directly cyclizing this formula III compound, it is preferred that the ester deprotection step described in Equation 4 is utilized prior to cyclization. In effect, a novel compound of formula IIIa is formed, and also is useful for the preparation of 5,6-dihydropyrrolo[2,3-d]pyrimidines.

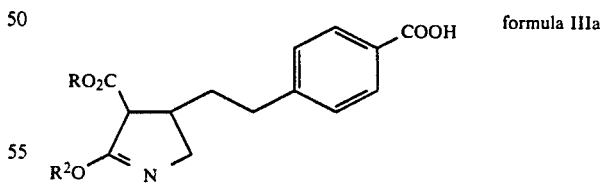

formula IIIa

The final reaction product of Equations 3, 4 and 5, a formula V compound, is easily converted to a therapeutically active 5,6-dihydropyrrolo[2,3-d]pyrimidine, or a derivative thereof, by conventional methods.

Generally a formula V compound is coupled with a protected L-glutamic acid derivative in the manner described in U.S. Pat. No. 4,684,653, using conventional condensation techniques for forming peptide bonds, but substituting the appropriate 5,6-dihydropyrrolo[2,3-d]pyrimidine for the pyrido[2,3-d]pyrimidine therein disclosed. The protected L-glutamic acid derivative is then subjected to hydrolysis to remove the remaining carboxyl protecting groups.

The following examples further illustrate the novel intermediate compounds, and processes thereto, according to the present invention. The examples are not intended to be limiting to the scope of the invention in any respect, and should not be so construed.

In the following examples, the terms melting point, nuclear magnetic resonance spectra, field desorption mass spectra, fast atom bombardment mass spectra, infrared spectra, ultraviolet spectra, elemental analysis, specific rotation, high performance liquid chromatography and thin layer liquid chromatography are abbreviated mp, NMR, MS(FD), MS(FAB), IR, UV, Anal., HPLC, and TLC, respectively. In addition, the adsorption maxima listed for the IR spectra are only those of interest and not necessarily all of the maxima observed.

The abbreviations THF and DMF stand for tetrahydrofuran and dimethylformamide, respectively.

The NMR spectra were obtained on a General Electric QE-300 300 MHz instrument. The chemical shifts are expressed in $\delta$ values (parts per million downfield from tetramethylsilane). The field desorption mass spectra were taken on a Varian-MAT 731 Spectrometer using carbon dendrite emitters Election Impact Mass Spectra were obtained on a CEC 21-110 instrument from Consolidated Electrodynamics Corporation. Infrared spectra were obtained on a Perkin-Elmer 281 instrument. Ultraviolet Spectra were obtained on Cary 118 instrument. Specific rotations were obtained on a Perkin-Elmer Q-41 instrument. Thin layer chromatography was carried out on E. Merck silica gel plates Melting points are uncorrected.

PREPARATION 1

3-(4-(2,2-dimethylethyl)carboxyphenyl)-1-propanal 44.57 Grams (0.147 mol) of t-butyl-4-iodobenzoate and 12.8 grams (0.221 mol) of allyl alcohol were mixed in 500 ml of dimethylformamide. Next, 1 gram (0.004 mol) of palladium(II) acetate, 30 8 grams (0.368 mol) of $NaHCO_3$, and 47.25 grams (0.147 mol) of tetrabutylammonium bromide were added to the mixture. This was stirred at room temperature under nitrogen for 72 hours. The reaction was deemed complete after this time period (TLC, silica, hexane-ether 3:2). The mixture was then poured into 2L of water and the resulting suspension was extracted with hexane (4 X 450 ml). The combined extracts were washed with water, then saturated NaCl solution, and finally dried ($Na_2SO_4$). Evaporation of the solvent afforded 33.7 grams of 3-(4-(2,2-dimethylethyl)carboxyphenyl)-1-propanal (98%) as an oil sufficiently pure for further processing. The crude material was purified for analysis by silica gel chromatography (hexane - ethyl acetate 7:3). Selected data: $^1H$ NMR ($CDCl_3$) $\delta$ 9.82 (s, 1H), 7.92 (d, J=9 Hz, 2H), 7.04 (d, J=9 Hz, 2H), 2.99 (t, J=7.8 Hz, 2H), 2.80 (t, J=7.8 Hz, 2H), 1.50 (s, 9H); $^{13}C$ NMR ($CDCl_3$) $\delta$ 200.8, 165.6, 145.3, 130.3, 129.8, 128.2, 80.9, 44.9, 28.2, 28.1; IR ($CHCl_3$) 1707 cm$^{-1}$, MS(FD) m/z 234 (M+); Anal. Calcd for $C_{14}H_{18}O_3$: C, 71.77; H, 7.74. Found: C, 71.72; H, 7.82.

PREPARATION 2

2-ethylcarboxy-5-(4-(2,2-dimethylethyl)carboxyphenyl)-2-pentenoic acid ethyl ester A mixture of 25.7 ml (45.14 g, 0.238 mol) of $TiCl_4$ in 57 ml $CCl_4$ was added dropwise to 475 ml of mechanically-stirring THF that had been cooled to −1.5° C. The mechanical stirring and dropwise addition were done to keep the temperature <3.5° C. The resulting yellow suspension was slowly combined with a second mixture of 27.8 grams (0.119 mol) of 3-(4-(2,2-dimethylethyl)carboxyphenyl)-1-propanal and 19 grams (0.119 mol) of diethyl malonate in 57 ml of dry THF. The combination is performed slowly to maintain a temperature <3° C. At this point, 38.3 ml (37.7 g, 0.476 ml) of dry pyridine were added to the newly combined mixtures This was stirred for 1 hour at 0°–3° C. and then allowed to come to room temperature overnight. The next day the mixture was mixed with 750 ml of water and extracted with 300 ml of ether. The aqueous phase was extracted with ether (2×250 ml) and the extracts were combined. The combined extracts were consecutively washed with 250 ml portions of water, 0.5 N HCl, water, saturated $NaHCO_3$, saturated NaCl and finally dried ($Na_2SO_4$). Evaporation of the solvent gave 43.3 grams (97%) of 2-ethylcarboxy-5-(4-(2,2-dimethylethyl)carboxyphenyl)-2-pentenoic acid ethyl ester as an oil, 85.7% pure (HPLC). Selected data: $^1H$ NMR ($CDCl_3$) $\delta$ 7.90 (d, J=8.1 Hz, 2H), 7 21 (d, J=8.1 Hz, 2H), 6.97 (t, J=8.4 Hz, 1H), 4.24 (m, 4H), 2.83 (t, J=7.1 Hz, 2H), 2.64 (t, J=7.1 Hz, 2H), 1.57 (s, 9H), 1.26 (m, 6H); IR (CHC13) 1710 cm-1, MS(FD) m/z 377 (M+). An analytical sample was prepared by flash chromatography (hexane - ethyl acetate 8:2). Anal. Calcd for $C_{21}H_{28}O_6$: C, 67.00; H, 7.50. Found: C, 67.06; H, 7.58.

EXAMPLE 1

2-ethylcarboxy-3-nitromethyl-5-(4-(2,2-dimethylethyl))-carboxyphenyl)-pentanoic acid ethyl ester A solution of 42.2 grams (0.113 mol) of 2-ethylcarboxy-5-(4-(2,2-dimethylethyl)carboxyphenyl)-2pentenoic acid ethyl ester in 150 ml of nitromethane and 1.5 grams of 1,8-diazabicyclo[5.4.0]undec-7-ene (DBU) was stirred at room temperature overnight. The reaction mixture was concentrated to a small volume, diluted with 300 ml of ether and with sufficient ethyl acetate to produce a clear solution The clear solution was consecutively washed with water, 0.5M HCl, water, saturated $NaHCO_3$, water, saturated NaCl and finally dried ($Na_2SO_4$). Evaporation of the solvent afforded 47.4 grams (96%) of 2-ethylcarboxy-3-nitromethyl-5-(4-(2,2-dimethylethyl)carboxyphenyl)-pentanoic acid ethyl ester as an oil. Flash chromatography (silica, hexane-ethyl acetate 1:4) of the crude provided 37 grams (75% based on 2-ethylcarboxy-5-(4-(2,2-dimethylethyl)carboxypheny)-2-acid ethyl ester) of purified 2-ethylcarboxy-3-nitromethyl-5-(4-(2,2-dimethylethyl)carboxyphenyl)-pentanoic acid ethyl ester. An analytical sample was prepared by additional flash chromatography. Selected data: $^1H$ NMR ($CDCl_3$) $\delta$ 7.90 (d, J=8.1 Hz, 2H), 7.18 (d, J=8.1 Hz, 2H), 4.74 (q, J=13.6, 4.9 Hz, 1H), 4.55 (q, J=13.6, 4.9 Hz, 1H), 4.20 (m, 4H), 3.64 (d, J=2.8 Hz, 1H), 2.92 (m, 1H), 2.74 (dd, J=8.3, 7.8 Hz, 2H), 1.80 (m,2H), 1.57 (s, 9H), 1.26 (m, 6H); IR ($CHCl_3$) 1746, 1729, 708 cm-1, MS(FD) m/z 437 (M+). Anal. Calcd for $C_{22}H_{31}NO_8$: C, 60.40; H, 7.14; N, 3.20 . Found: C, 60.45; H, 7.26; N, 2.99.

EXAMPLE 2

4-(2-(2-oxo-3-carboethoxypyrrolidin-4-yl)ethyl)benzoic acid, 2,2-dimethylethyl ester A mixture of 10.32 grams of 2-ethylcarboxy-3-nitromethyl-5-(4-(2,2-dimethylethyl)carboxyphenyl)- pentanoic acid ethyl ester and 1.5 grams of platinum-(IV) oxide in 200 ml of ethanol was hydrogenated in a Parr apparatus at an initial pressure of 50 psig H2. Filtration of the catalyst and removal of the solvent in vacuo provided the crude product as an oil which crystallized upon dissolution in 50 ml ether and addition of about 200 ml hexane until just cloudy. After stirring overnight, the crystalline material was filtered, washed with hexane, dried; affording 3.54 grams (42%) of 4-(2-(2-oxo-3-carboethoxypyrrolidin-4-yl)ethyl)benzoic acid, 2,2-dimethylethyl ester. Selected data: mp 98°–104° C., $^1$H NMR (CDCl$_3$) δ 7.89 (d, J=8.2 Hz, 2H), 7.18 (d, J=8.2 Hz, 2H), 6.75 (s, 1H), 4.23 (q, 2H), 3.54 (dd, J=9.0, 8.3 Hz, 1H), 3.12 (d, J=8.6 Hz, 1H), 3.00 (dd, J=9.4, 7.4 Hz, 1H), 2.87 (m, 1H), 2.66 (t, J=7.6 Hz, 2H), 1.86 (m, 2H), 1.57 (s, 9H), 1.28 (t, 3H); $^{13}$C NMR (CDCl$_3$) δ 173.2, 169.7, 165.6, 145.8, 130.1, 129.7, 128.0, 80.8, 62.6, 54.4, 46.5, 38.9, 35.1, 32.4, 28.1, 14.1; MS(FAB) m/z 362 (7, M$^+$+1), 306 (100), 288 (22), Anal. Calcd for C$_{20}$H$_{27}$NO$_5$: C, 66.46; H, 7.53; N, 3.87. Found: C, 66.44; H, 7.77; N, 3.86.

EXAMPLE 3

4-(2-[2-iminomethoxy-3-carboethoxy-3H-4,5-dihydropyrrol-4-yl]ethyl)benzoic acid, 2,2-dimethylethyl ester A mixture Of 3.61 grams (10 mmol) of 4-(2-(2-oxo-3-carboethoxypyrrolidin-4-yl)ethyl)benzoic acid, 2,2-dimethylethyl ester and 5.03 grams (60 mmol) of NaHCO$_3$ in 115 ml of chloroform under nitrogen was combined with 4.43 grams (30 mmol) of trimethyloxonium tetrafluoroborate, the transfer being completed with 50 ml of additional chloroform. After stirring at room temperature for 4 hours, 40 ml of water were added and the layers separated. The aqueous phase was extracted with 40 ml of chloroform and the organic phases combined and dried (MgSO$_4$). Evaporation of the solvent in vacuo afforded 4.0 grams of crude 4-(2-[2-iminomethoxy-3-carboethoxy-3H-4,5-dihydropyrrol-4-yl]ethyl)-benzoic acid, 2,2-dimethylethyl ester as an oil. Purification by flash chromatography (silica gel, ether-hexane 4:1, ether, and ethyl acetate successively) provided purified 4-(2-[2-iminomethoxy-3-carboethoxy-3H-4,5-dihydropyrrol-4-yl]ethyl)benzoic acid, 2,2-dimethylethyl ester as a clear, viscous oil. Selected data: $^1$H NMR (CDCl$_3$) δ 7.83 (d, J=8.1 Hz, 2H), 7.13 (d, J=8.1 Hz, 2H), 4.14 (q, 2H), 3.82 (m, 1H), 3.75 (s, 3H), 3.26 (m, 2H), 2.71 (m, 1H), 2.60 (m, 2H), 1.77 (m, 2H), 1.52 (s, 9H), 1.22 (t, 3H).

EXAMPLE 4

4-(2-[2-iminomethoxy-3-carboethoxy-3H-4,5-dihydropyrrol-4-yl]ethyl)benzoic acid

A mixture of 580 mg (1.54 mmol) of 4-(2-[2-iminomethoxy-3-carboethoxy-3H-4,5-dihydropyrrol-4-yl]ethyl)-benzoic acid, 2,2-dimethylethyl ester and 10 ml of trifluoroacetic acid was stirred for 2 minutes to affect complete solution then immediately concentrated to dryness in vacuo. The residue was taken up in 2 ml of methanol and the resulting solution was slowly added to 15 ml saturated aqueous sodium bicarbonate so as to keep the pH of the solution in the range 7.1–7.6. The pH of the resulting mixture was adjusted to 5.5 by addition of acetic acid and the product was extracted with 3×10 ml ethyl acetate. The organic extracts were combined and dried (MgSO$_4$) and concentrated to give 498 mg (100%) of 4-(2-[2-iminomethoxy-3-carboethoxy-3H-4,5-dihydropyrrol-4-yl]ethyl)benzoic acid as an amorphous material Selected data $^1$H NMR (CDCl$_3$) δ 8.00 (d, J=8.0 Hz, 2H), 7.24 (d, J =8.0 Hz, 2H), 4.27 (q, 2H) 3.93 (m, 1H), 3.84 (s, 3H), 3.35 (m, 2H), 2.90 (m, 1H), 2.79 (m, 2H), 1.86 (m, 2H), 1.28 (t, 3H).

EXAMPLE 5

4-(2-[2-amino-4,5,6,7-tetrahydro-4-oxo-3H-pyrrolo[2,3-d]pyrimidin-5-yl]ethyl)benzoic acid A solution of sodium ethoxide in ethanol (prepared by cautious addition of 120 mg (5.0 meq) sodium hydride to 10 ml of anhydrous ethanol) was combined with 477 mg (5.0 mmol) of guanidine hydrochloride and the resulting mixture was heated to 50° C. for 20 min. The precipitated salt was filtered and 404 mg (1.27 mmol) of 4-(2-[2-iminomethoxy-3-carboethoxy-3H-4,5-dihydropyrrol-4-yl]ethyl)benzoic acid was added to the resulting solution. The mixture was stirred until clear and then concentrated in vacuo to remove most of the alcohol. The mixture was heated to 90° C. at 10 torr for 90 min, then cooled to room temperature and diluted with 10 ml of water. The product was precipitated by addition of 6M HCl to a pH of 5.5 and then filtered. The precipitate was consecutively washed with water, ethanol, and ether and vacuum dried at 50° C., affording 218 mg (58%) of 4-(2-[2- amino-4,5,6,7-tetrahydro- 4-oxo-3H-pyrrolo[2,3-d]pyrimidin-5-yl]ethyl)benzoic acid as an amorphous solid. Selected data: mp <290° C.; $^1$H NMR (CDC$_3$) δ 13 (bs, 1H), 9.6 (bs, 1H), 7.79 (d, J=8.2 Hz, 2H), 7.27 (d, J=8.2 Hz, 2H), 6.29 (s, 1H), 6.23 (s, 2H), 3.44 (t, J=8.6 Hz, 1H), 3.03 (m, 2H), 2.62 (t, J =7.7 Hz, 2H), 2.00 (m, 1H), 1.54 (m, 1H); IR (KBr) 3427, 3328, 3140, 2910, 1643, 1574, 1264 cm$^{-1}$. HRMS (FAB) m/z calcd for C$_{15}$H$_{17}$N$_4$O$_3$ (MH+):301.1301. Found:301.1298.

EXAMPLE 6

4-(2-[2-thiocarbonyl-3-carboethoxypyrrolidin-4-yl]ethyl)benzoic acid 2,2-dimethylethyl ester A mixture of 5.10 grams (14.1 mmol) of 4-(2-(2-oxo-3-carboethoxypyrrolidin-4-yl)ethyl)benzoic acid, 2,2-dimethylethyl ester and 3.45 grams (7.76 mmol) of phosphorus pentasulfide in 150 ml of THF was stirred at 60° C. for 30 min, cooled, and filtered The solvent was then removed by vacuum evaporation. The crude product thusly obtained was purified by flash chromatography (silica, EtOAc-hexane 1:1), affording 4.11 grams (77%) of 4-(2-[2-thiocarbonyl-3-carboethoxypyrrolidin-4-yl]ethyl)benzoic acid 2,2-dimethylethyl ester as an oil. Selected data: $^1$H NMR (CDCl$_3$) δ 7.97 (bs, 1H), 7.90 (d, J=8.2 Hz, 2H), 7.18 (d, J =8.2 Hz, 2H), 4.26 (m, 2H), 3.82 (m, 1H), 3.53 (d, J=7.2 Hz, 1H), 3.28 (dd, J=10.8, 6.5.Hz, 1H), 2.90 (m, 1H), 2.68 (m, 2H), 1.85 (m, 2H), 1.57 (s, 9H), 1.31 (t, 3H); IR (CHCl$_3$) 2983, 1732, 1707, 1517, 1471, 1393, 1371, 1313, 1297, 1166, 1121 cm$^{-1}$; HRMS (FAB) m/z calcd for C$_{20}$H$_{28}$NO$_4$S: 378.1739; Found: 378.1729.

EXAMPLE 7

4-(2-(2-thiocarbonyl-3-carboethoxypyrrolidin-4-yl)ethyl)benzoic acid

A mixture of 4.17 grams (11.1 mmol) of 4-(2-[2-thiocarbonyl-3-carboethoxypyrrolidin-4-yl]ethyl)benzoic acid 2,2-dimethylethyl ester and 20 ml of trifluoroacetic acid was stirred at room temperature until a clear solution was obtained plus an additional 5 minutes. Next, the resulting mixture was concentrated in a rotary evaporator and the residue therefrom was dissolved in 10 ml of methanol. This new solution was carefully added to a suspension of 2 grams of NaHCO$_3$ in saturated NaHCO$_3$ solution. The pH was adjusted to 5.7 with acetic acid and the resulting mixture extracted with 5×20 ml of ethyl acetate. The combined extracts were dried (MgSO$_4$) and then concentrated to give 3.87 grams (109% crude yield) of 4-(2-(2-thiocarbonyl-3-carboethoxypyrrolidin-4-yl)ethyl)benzoic acid as a foam which was sufficiently pure for use in Example 8. Crystalline 4-(2-(2-thiocarbonyl-3-carboethoxypyrrolidin-4-yl)ethyl)benzoic acid was obtained from chloroform. Selected data: mp 145°–148° C.; $^1$H NMR DMSO-d$_6$) δ 10.39 (s, 1H), 7.80 (d, J=8.1 Hz, 2H), 7.24 J=8.1 Hz, 2H), 4.06 (q, J=7.1 Hz, 2H), 3.64 (dd, J=10.9, 8.9 Hz, 1H), 3.46 (d, J =8.5 Hz, 1H), 3.20 (dd, J=10.9, 8.0 Hz, 1H), 2.64 (q, J =8.0 Hz, 1H), 2.54 (t, J=7.4 Hz, 2H), 1.70 (m, 2H), 1.12 (t, J=7.1 Hz, 3H); $^{13}$C NMR (DMSO-d6) δ 198.6, 169.5, 167.0, 146.2, 129.1, 128.6, 128.1, 65.0, 60.4, 52.9, 40.8, 33.5, 32.6, 13.7; IR (CHCl$_3$) 3410, 2985, 1732, 1694, 1517 cm$^{-1}$; UV (EtOH) 236 nm (ε 14 900), 271 (15 600); MS(FD) m/z 321 (M+). Anal. Calcd for C$_{16}$H$_{19}$NO$_4$S: C, 59.79; H, 5.96; N, 4.36. Found: C, 59.77; H, 6.00; N, 4.37.

EXAMPLE 8

4-(2-[2-amino-4,5,6,7-tetrahydro-4-oxo-3H-pyrrolo[2,3-d]pyrimidin-5-yl]ethyl)benzoic acid A solution of sodium ethoxide in ethanol [prepared by reaction of 1.06 grams (44.1 mmol) of sodium hydride and 50 ml of ethanol] was combined with 4.22 grams (44.1 mmol) of guanidine HCl and then stirred at 50° C. for 20 minutes. The cooled suspension was filtered (celite) to remove NaCl and the filtrate was mixed with 2.83 grams (8.81 mmol) of 4-(2-(2-thiocarbonyl-3-carboethoxypyrrolidin-4-yl)ethyl)benzoic acid. The resulting solution was concentrated in vacuo to remove most of the alcohol and the residue was slowly heated to 90° C. while maintaining a vacuum of 10 torr. After heating 1 additional hour, the mixture was cooled and the reaction product taken up in 75 ml of water. The pH of the mixture was adjusted to 6 by addition of 6M HCl and the mixture was then filtered. The precipitate was consecutively washed with 20 ml water, 20 ml methanol, and 40 ml ether. After drying, 2.13 grams (64%) of 4-(2-[2-amino-4,5,6,7-tetrahydro-4-oxo-3H-pyrrolo[2,3-d]pyrimidin-5yl]ethyl)benzoic acid was obtained.

EXAMPLE 9

N-[4-[2-(2-amino-4,5,6,7-tetrahydro-4-oxo-3H-pyrrolo[2,3-d]pyrimidin-5-yl)ethyl]benzoyl]-L-glutamic acid diethyl ester 1.12 Grams (6.36 mmol) of chlorodimethoxytriazine was added to a solution of 1.91 grams (6.36 mmol) of 4-(2-[2-amino-4,5,6,7-tetrahydro-4-oxo-3H-pyrrolo[2,3-d]pyrimidin-5-yl]ethyl)benzoic acid and 0.63 grams (6.3 mmol) of N-methylmorpholine (NMM) in 20 ml of dimethylformamide (DMF) at room temperature. The resulting mixture was stirred at room temperature for 2 hours. Next, an additional 0.3 grams (2.97 mmol) of NMM and 0.22 grams (1.25 mmol) of chlorodimethoxytriazine was added to the solution and the mixture stirred for an additional 30 min. Then, 0.64 grams (6.3 mmol) of NMM and 1.52 grams (6.3 mmol) of diethyl-L-glutamate hydrochloride was added to the mixture. After stirring overnight at room temperature, the resulting suspension was mixed with 30 grams of silica gel and dried under vacuum. The residue was added to a column of 70 grams silica gel and eluted with 500 ml of CH$_2$Cl$_2$-EtOH 90:10 followed by CH$_2$Cl$_2$-EtOH 80:20. 1.62 Grams (52%) of purified N-[4-[2-(2-amino-4,5,6,7-tetrahydro-4-oxo 3H-pyrrolo[2,3-d]pyrimidin-5-yl)ethyl]benzoyl]-L-glutamic acid diethyl ester was obtained as a colorless powder. Selected data: $^1$H NMR (DMSO-d6) δ 9.55 (s, 1H), 8.60 (d, J=7.4 Hz, 1H), 7.73 (d, J=8.3 Hz, 2H) 7.27 (d, J=8.3 Hz, 2H), 6.28 (s, 1H), 6.20 (s, 2H), 4.38 (m, 1H), 4.05 (q, J=7.1 Hz, 2H), 3.99 (q, J=7.1 Hz, 2H), 3.40 (m, 1H), 3.02 (m, 2H), 2.65 (t, J=7.6 Hz, 2H), 2.39 (t, J=7.5 Hz, 2H), 2.00 (m, 3H), 1.54 (m, 1H), 1.13 (t, J =7.1 Hz, 3H), 1.11 (t, J=7.1 Hz, 3H).

EXAMPLE 10

N-[4-[2-(2-amino-4,5,6,7-tetrahydro-4-oxo-3H-pyrrolo[2,3-d]pyrimidin-5-yl)ethyl]benzoyl]-L-glutamic acid A solution of 1.50 grams (3.09 mmol) of N-[4-[2-(2-amino-4,5,6,7-tetrahydro-4-oxo-3H-pyrrolo[2,3-d]pyrimidin-5-yl)ethyl]benzoyl]-L-glutamic acid diethyl ester in 25 ml 1N NaOH was stirred at room temperature for 3 hours. The solution was carefully acidified to a of pH 2.8 by addition of 6M aqueous HCl and the resulting suspension was then filtered The precipitate was consecutively washed with 20 ml water, 10 ml methanol, 10 ml ether, and dried overnight at 50° C. and 10 torr. 1.13 g (85% of theory) of N-[4-[2-(2-amino-4,5,6,7-tetrahydro-4-oxo-3H-pyrrolo[2,3-d]pyrimidin-5-yl)ethyl]benzoyl]-L-glutamic acid was obtained as an amorphous solid. Selected data: $^1$H NMR (DMSO-d6) δ 12.20 (bs, 2H), 9.83 (bs, 1H), 8.48 (d, J=7.7 Hz, 1H), 7.74 (d, J=8.1 Hz, 2H), 7.26 (d, J=8.1 Hz, 2H), 6.32 (bs, 2H), 6.28 (bs, 1H), 4.33 (m, 1H), 3.43 (m, 1H), 3.01 (m, 2H), 2.61 (t, J=8.0 Hz, 2H), 2.30 (t, J=7.4 Hz, 2H), 1.96 (m, 3H), 1.54 (m, 1H); $^{13}$C NMR (DMSO-d6) δ 173.7, 173.1, 169.4, 166.5, 159.0, 156.7, 146.2, 131.4, 127.9, 127.2, 89.1, 52.1, 49.3, 36.9, 35.5, 32.3, 30.5, 26.2; IR (KBr) 3366, 2931, 1639, 1503, 1451, 1091 cm$^{-1}$; MS(FAB) m/z 430 (MH+); UV (EtOH) 220 nm (ε 27 660), 280 (11 300).

We claim:

1. A compound of formula II

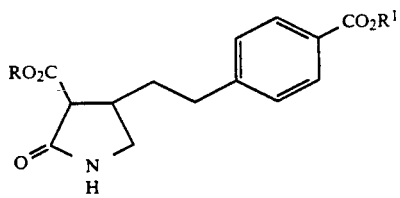

wherein

R is C$_1$–C$_4$ alkyl or phenyl which may be substituted; and

R$^1$ is H, C$_1$–C$_4$ alkyl, phenyl which may be substituted or benzyl; or a salt thereof.

2. A compound according to claim 1 wherein R is ethyl.

3. A compound according to claim 1 wherein R$^1$ is t-butyl.

4. A compound according to claim 3 wherein R is ethyl.

5. A compound of formula III

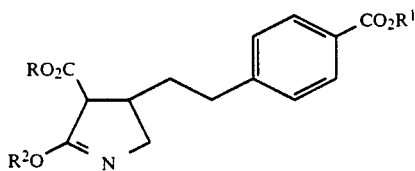

III wherein
R is $C_1$-$C_4$ alkyl or phenyl which may be substituted; and
$R^1$ is H, $C_1$-$C_4$ alkyl, phenyl which may be substituted or benzyl; and
$R^2$ is $C_1$-$C_4$ alkyl; or a salt thereof.

6. A compound according to claim 5 wherein R and $R^2$ are ethyl.

7. A compound according to claim 5 wherein $R^1$ is t-butyl.

8. A compound according to claim 7 wherein R and $R^2$ are ethyl.

9. A compound of formula IV

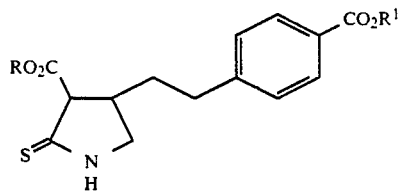

IV wherein
R is $C_1$-$C_4$ alkyl or phenyl which may be substituted; and
$R^1$ is H, $C_1$-$C_4$ alkyl, phenyl which may be substituted or benzyl; or a salt thereof.

10. A compound according to claim 9 wherein R is ethyl.

11. A compound according to claim 9 wherein $R^1$ is t-butyl.

12. A compound according to claim 11 wherein R is ethyl.

13. A compound according to claim 9 wherein $R^1$ is H.

14. A compound according to claim 13 wherein R is ethyl.

* * * * *